(12) United States Patent
Weiner et al.

(10) Patent No.: US 7,517,350 B2
(45) Date of Patent: Apr. 14, 2009

(54) CONVERTIBLE THREADED COMPRESSION DEVICE AND METHOD OF USE

(75) Inventors: Lon S. Weiner, Rumson, NJ (US); Thomas Coull, Rancho Palos Verdes, CA (US)

(73) Assignee: OrthoPediatrics Corp., Warsaw, IN (US)

( * ) Notice: Subject to any disclaimer, the term of this patent is extended or adjusted under 35 U.S.C. 154(b) by 660 days.

(21) Appl. No.: 10/790,342

(22) Filed: Mar. 1, 2004

(65) Prior Publication Data

US 2004/0167519 A1 Aug. 26, 2004

Related U.S. Application Data

(63) Continuation-in-part of application No. 10/300,078, filed on Nov. 20, 2002.

(60) Provisional application No. 60/503,565, filed on Sep. 17, 2003.

(51) Int. Cl.
*A61B 17/88* (2006.01)
(52) U.S. Cl. ........................ 606/105; 606/307; 606/310
(58) Field of Classification Search .................. 606/65, 606/72, 73, 86
See application file for complete search history.

(56) References Cited

U.S. PATENT DOCUMENTS

| | | | |
|---|---|---|---|
| 2,393,694 A | 1/1946 | Kirschner | |
| 2,760,488 A * | 8/1956 | Pierce | 606/73 |
| 4,175,555 A | 11/1979 | Herbert | 128/92 |
| 4,450,835 A * | 5/1984 | Asnis et al. | 606/96 |
| 4,456,005 A * | 6/1984 | Lichty | 606/60 |
| 4,463,753 A | 8/1984 | Gustilo | 128/92 |
| 4,616,638 A * | 10/1986 | Griggs | 606/104 |
| 4,628,921 A | 12/1986 | Rousso | 128/92 Z |
| 4,723,541 A | 2/1988 | Reese | 128/92 |

(Continued)

FOREIGN PATENT DOCUMENTS

WO WO 92/04875 4/1992

(Continued)

OTHER PUBLICATIONS

Depuy/Johnson & Johnson Gateway, LLC, "Rockwood Clavicle Pin", www.jnjgateway.com, 2 pages.

(Continued)

*Primary Examiner*—Eduardo C Robert
*Assistant Examiner*—Jerry Cumberledge
(74) *Attorney, Agent, or Firm*—Matthew R. Schantz; Bingham McHale LLP

(57) ABSTRACT

A convertible threaded compression device connects a bone fragment to an anchor bone for a healing duration. The compression device has a distal bone penetration section which is advanced into the bone and a proximal bone exterior section. The proximal bone exterior section is longer than the bone penetration section. The bone penetration section includes a distal bone anchor section which threadingly engages the anchor bone, and a proximal fragment section which fits within the overbore created by the bone anchor section. A compression engagement on a distal end of the bone exterior section provides a compression shoulder. The shoulder makes substantial contact with an exterior surface of the bone fragment, biasing the bone fragment toward the anchor bone with a controlled compression force. The compression engagement enables the device to be easily removed from the healed fracture without damaging surrounding tissue.

1 Claim, 4 Drawing Sheets

U.S. PATENT DOCUMENTS

| | | | | |
|---|---|---|---|---|
| 4,854,311 | A | 8/1989 | Steffee | 128/92 YM |
| 4,858,601 | A | 8/1989 | Glisson | 128/92 R |
| RE33,348 | E | 9/1990 | Lower | 606/65 |
| 4,964,403 | A | 10/1990 | Karas et al. | |
| 5,019,079 | A | 5/1991 | Ross | 606/72 |
| 5,122,133 | A * | 6/1992 | Evans | 606/301 |
| 5,139,500 | A | 8/1992 | Schwartz | 606/96 |
| 5,180,382 | A | 1/1993 | Frigg et al. | 606/65 |
| 5,226,766 | A | 7/1993 | Lasner | 411/308 |
| 5,242,443 | A * | 9/1993 | Kambin | 606/60 |
| 5,259,398 | A | 11/1993 | Vrespa | 128/898 |
| 5,403,136 | A | 4/1995 | Mathys | 411/310 |
| 5,409,486 | A | 4/1995 | Reese | 606/73 |
| 5,417,533 | A | 5/1995 | Lasner | 411/126 |
| 5,492,442 | A | 2/1996 | Lasner | 411/426 |
| 5,562,661 | A | 10/1996 | Yoshimi et al. | 606/61 |
| 5,562,672 | A | 10/1996 | Huebner et al. | 606/73 |
| 5,580,352 | A | 12/1996 | Sekel | 623/23 |
| 5,609,595 | A | 3/1997 | Pennig | 606/73 |
| 5,653,710 | A * | 8/1997 | Harle | 606/73 |
| 5,709,687 | A | 1/1998 | Pennig | 606/73 |
| 5,871,486 | A | 2/1999 | Huebner et al. | 606/73 |
| 5,957,927 | A * | 9/1999 | Magee et al. | 606/99 |
| 5,964,768 | A | 10/1999 | Huebner | 606/73 |
| 5,968,046 | A | 10/1999 | Castleman | 606/73 |
| 5,989,255 | A * | 11/1999 | Pepper et al. | 606/73 |
| 6,001,101 | A | 12/1999 | Augagneur et al. | 606/73 |
| 6,030,162 | A * | 2/2000 | Huebner | 411/413 |
| 6,099,529 | A | 8/2000 | Gertzman et al. | 606/73 |
| 6,129,730 | A | 10/2000 | Bono et al. | 606/73 |
| 6,159,210 | A | 12/2000 | Voor | 606/56 |
| 6,162,225 | A | 12/2000 | Gertzman et al. | 606/73 |
| 6,238,417 | B1 | 5/2001 | Cole | 606/213 |
| 6,261,292 | B1 | 7/2001 | Diebold et al. | 606/73 |
| 6,306,140 | B1 | 10/2001 | Siddiqui | 606/73 |
| 6,348,053 | B1 | 2/2002 | Cachia | 606/72 |
| 6,388,732 | B1 | 10/2002 | Yang | |
| 6,511,481 | B2 * | 1/2003 | von Hoffmann et al. | 606/67 |
| 6,632,224 | B2 | 10/2003 | Cachia et al. | 606/72 |
| 6,648,890 | B2 | 11/2003 | Culbert et al. | 606/63 |
| 6,685,706 | B2 | 2/2004 | Padget et al. | 606/72 |
| 2002/0143335 | A1 | 10/2002 | von Hoffmann et al. | |
| 2003/0158556 | A1 * | 8/2003 | Taras et al. | 606/73 |

FOREIGN PATENT DOCUMENTS

| | | |
|---|---|---|
| WO | WO 00/40164 | 7/2000 |

OTHER PUBLICATIONS

Depuy/Johnson & Johnson Gateway, LLC,, "Bone Screws and Pins, Essential Product Information", www.jnjgateway.com, 2 pages.
Depuy/Johnson & Johnson Gateway, LLC, "Rockwood Clavicle Pin, Case X-Rays", www.jnjgateway.com, 2 pages.
Depuy/Johnson & Johnson Gateway, LLC, "Rockwood Clavicle Pin, Design Rationale", www.jnjgateway.com, 2 pages.
Depuy/Johnson & Johnson Gateway, LLC, "Rockwood Clavicle Pin, Surgical Technique", www.jnjgateway.com, 11 pages.
Depuy/Johnson & Johnson Gateway, LLC, "Rockwood Clavicle Pin, Post Operative Care", www.jnjgateway.com, 2 pages.
Beaumont Hospitals, "Athletes pinning their hopes on new procedure", www.beaumonthospitals.com, 2 pages.
Wheeless, "IM Pin Fixation of Clavicle Frx", www.wheelessonline.com, 4 pages.
Fabory Catalog pp. 4-39, "Dowel Screws".

* cited by examiner

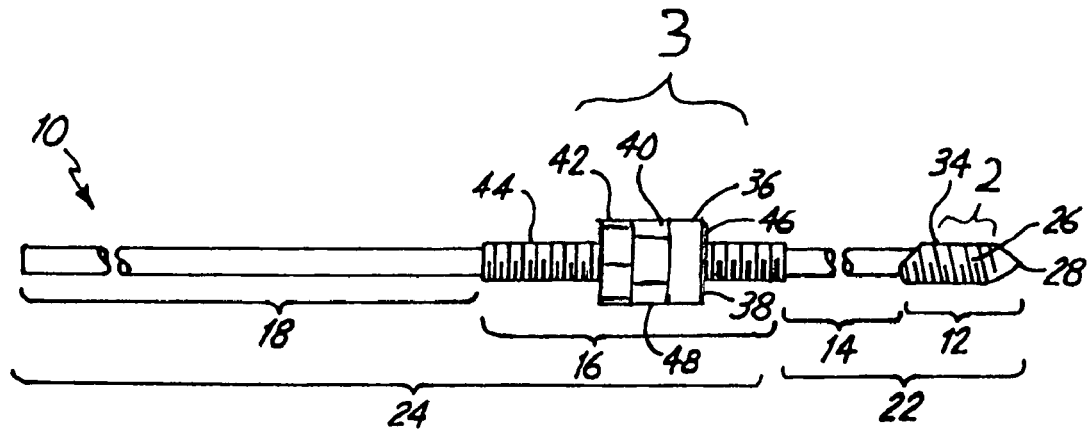
Fig. 1
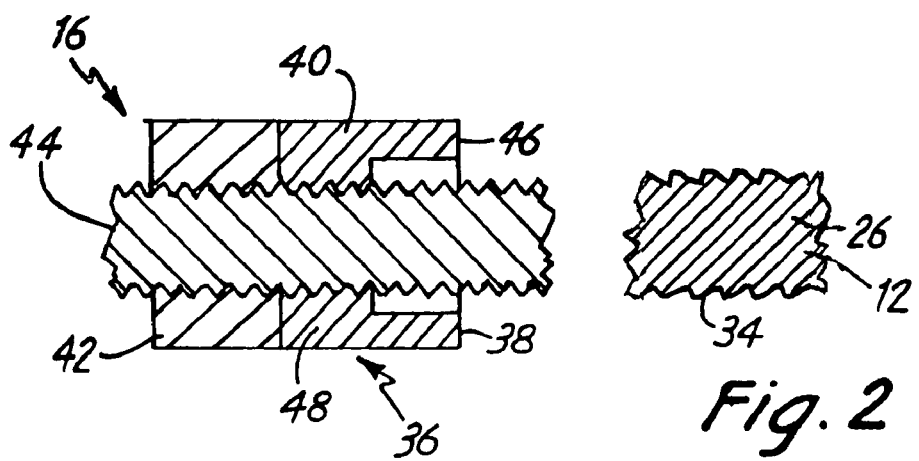
Fig. 3
Fig. 2

CONVERTIBLE THREADED COMPRESSION DEVICE AND METHOD OF USE

CROSS-REFERENCE TO RELATED APPLICATION(S)

This is a continuation-in-part of application Ser. No. 10/300,078 filed Nov. 20, 2002, entitled COMPRESSION BONE FRAGMENT WIRE, now pending. This application also claims priority from Provisional Application No. 60/503,565 filed Sep. 17, 2003, entitled PERCUTANEOUS COMPRESSION BONE FRAGMENT DEVICE.

BACKGROUND OF THE INVENTION

The present application is directed to bone pins and wires, and, more specifically, to bone pins and wires used to attach a bone fragment to an anchor bone for a healing duration. Further, the present application is directed to bone screws which are used to attach a bone fragment to an anchor bone for a healing duration, and to a method of using such bone pins, wires and screws, which may involve manipulating the bone fragment relative to the anchor bone during the fixation surgery.

Bone pins and wires are characterized by having a relative small diameter, such as a diameter of 0.1 inches (2.5 mm) or less. Bone pins which are elongated wires are commonly referred to as "Kirschner wires" or "K-wires". An example of this is disclosed in U.S. Pat. No. 2,393,694 to Kirschner. The term "bone pin" is more commonly used for shorter structures, such as a length of 2 inches or less, while the term "K-wire" more commonly applies to longer structures, such as a length up to 12 inches, but there is no bright line definition clearly distinguishing between a "bone pin" and a "K-wire" based on length. The present application uses the term "bone wire" to refer to such a small diameter structure and including either a bone pin or a K-wire, regardless of length, but excluding, for instance, a larger diameter bone screw. The present application uses the term "bone screw" to refer to threaded bone fixation devices having a diameter greater than 0.1 inches (2.5 mm).

Bone wires have long been used in the orthopaedic arts for several different purposes. Bone wires are often used during surgery as a temporary guide in targeting and directing another more permanent device, such as a cannulated bone screw running over the bone wire, into a bone fragment or anchor bone. Bone wires have been implanted to anchor other devices, such as a bone plate, fixator or external splint device, to a fractured bone. Bone wires have also been used to secure many types of bone fragments to anchor bones, where the term bone "fragment" refers to any part of bone separated by a fracture, regardless of whether that fracture is partial or completely through the bone.

Bone wires commonly have a pointed tip, which may be further fabricated with a drill type structure such that rotation of the bone wire about its longitudinal axis helps to remove bone material from the hole into which the bone wire is advanced. The bone wires may or may not have fine threads to further assist in axially advancing the bone wire into its hole during rotation. While bone wires have been used for fragment fixation, design improvements are needed to have a small diameter bone wire structure which more easily places an appropriate compression force on the interface between the bone fragment and its anchor bone.

Bone screws have also long been used in the orthopaedic arts. Bone screws are typically used for permanent or semi-permanent fixation, either attaching a larger bone fragment to an anchor bone, or attaching a stress-supporting fixation device, such as a bone plate or intramedullary nail, to an anchor bone. Many different constructions of bone screw are known. The bone screws can have specific thread designs, including self-tapping threads distally for insertion and self-tapping threads proximally for extraction. The bone screws can have heads of specific designs, such as to induce rotation or pivoting of the bone screw upon advancement or retraction. Bone screws are typically fabricated at a diameter to support the torque with which the bone screw will be advanced as well as the shear forces to which the bone screw will likely be subjected. Bone screws are typically selected at a length dependent upon the location and orientation of use, such that the entire bone screw during use will reside within the profile of the patient's tissue.

BRIEF SUMMARY OF THE INVENTION

The present invention is a threaded wire or screw which can be used for connecting a fragment in compression to an anchor substrate, such as a bone fragment to an anchor bone for a healing duration. The compression device has a penetration section which is advanced into the fragment/substrate. The penetration section includes a distal anchor section which threadingly engages the anchor substrate, and a fragment section which extends through but does not positively engage the fragment. The fragment section thus fits within the overbore created by advancing the distal anchor section through the fragment. The compression device has an exterior section which may extend substantially out of the fragment/substrate during use. In particular as applied to a bone fragment compression device, the bone exterior section has a length sufficient for percutaneous use. A compression engagement on a distal end of the exterior section provides a compression shoulder. The shoulder makes substantial contact with an exterior surface of the fragment, biasing the fragment toward the anchor substrate with a controlled compression force.

In one aspect as a bone fragment compression device, the length of the bone exterior section is sufficient that the surgeon can use the compression device in a novel and non-obvious method of attachment. After the device has been advanced such that the bone anchor section resides in the bone fragment but before the bone anchor section penetrates the anchor bone, the surgeon can use the bone exterior section in a "joystick" operation to move the bone fragment and bias the bone fragment into position as desired against the anchor bone. The surgeon can then percutaneously hold the bone exterior section in the desired alignment during advancement of the bone anchor section into the anchor bone. If desired, the bone exterior section can be clipped after the device has been fully advanced and anchored into the anchor bone.

BRIEF DESCRIPTION OF THE DRAWINGS

FIG. 1 is a side view of a first embodiment of the invention.

FIG. 2 is a cross sectional view of the threads/nuts taken at area 2 of FIG. 1.

FIG. 3 is a cross sectional view of the threads taken at area 3 of FIG. 1.

Figure 4:
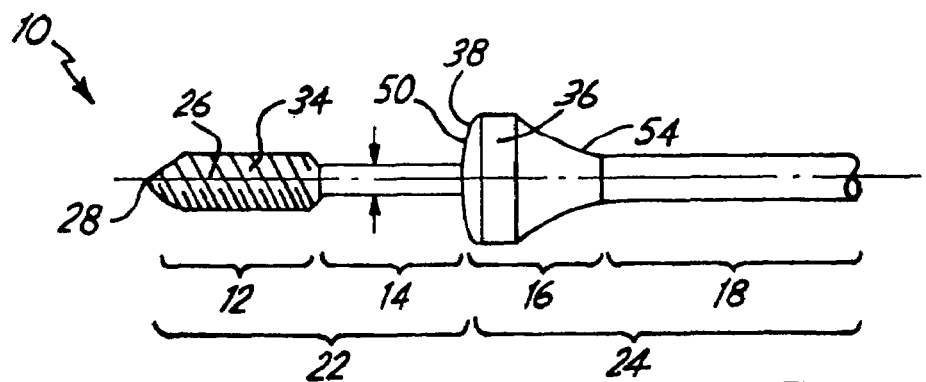
FIG. 4 is a side view of the second embodiment of the invention.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

A preferred convertible threaded compression device or CTCD 10 of the present invention includes an anchor section 12 located distally of an intermediate fragment section 14. A compression section 16 is provided proximally of the intermediate fragment section 14, and a rotation section 18 is provided proximally of the compression section 16. While the CTCD 10 has many applications of connecting a fragment to an anchor substrate other than bone, the CTCD 10 has several features which make it particularly advantageous for orthopaedic applications, and the CTCD 10 will be generally described in its orthopaedic use. In the surgical method of using the CTCD 10, the anchor section 12 and the fragment section 14 penetrate the bone 20, while the compression section 16 and the rotation section 18 remain outside on the exterior of the bone 20.

Preferably, the anchor section 12 is shorter than the combined length of the bone exterior section 24, i.e., the compression section 16 and the rotation section 18. More preferably, the entire bone penetrating section 22, i.e., the anchor section 12 and the fragment section 14, are shorter in combined length than the combined length of the bone exterior section 24, i.e., the compression section 16 and the rotation section 18. Additionally, the preferred rotation section 18 makes up at least one third of the entire length of the CTCD 10. More preferably, the rotation section 18 makes up 45% or more of the entire length of the CTCD 10. Most preferred lengths for the anchor section 12, the fragment section 14, the compression section 16 and the rotation section 18 are provided below in Table I.

The distal anchor section 12 has a shaft portion 26 terminating in a drill tip 28. The hole which is made in the fragment 30 and the anchor bone 32 for the CTCD 10 is generally not pre-drilled, but rather is drilled by the drill tip 28 during advancement of the CTCD 10 through the fragment 30 and into the anchor bone 32. By using the drill tip 28 to drill the hole rather than pre-drilling, the duration of the insertion procedure is shortened, which is particularly important during surgical applications for minimizing both the trauma to the patient and the cost of the procedure. Alternatively, the hole can be pre-drilled in the fragment 30 and/or the anchor bone 32, particularly for larger diameter CTCDs, but the pre-drilled hole is preferably the size of or smaller than the minor diameter of the distal anchor section 12. The drill tip 28 may be constructed in accordance with drill tip techniques used on current bone wires and bone screws, such as a three-sided sharp trocar. As known in the art, this drill tip 28 assists the CTCD 10 in drilling a hole through bone 20, breaking up bone and removing bone powder and minute bone pieces from the hole during drilling.

The shaft portion 26 includes anchor threads 34, which serve both to advance the CTCD 10 into the anchor bone 32 during rotation, and to anchor the CTCD 10 into the anchor bone 32 after implantation is completed. The shaft portion 26 has a relatively short length suitable for anchoring in a desired anchor bone 32. The shaft portion 26 of the distal anchor section 12 may have a length in the range of about 5 to 10 mm for about a five to ten millimeter anchor. During orthopaedic use, the CTCD 10 is advanced through a fragment 30 and into an anchor bone 32 until the distal anchor section 12 is substantially entirely within the anchor bone 32. The anchor threads 34 are constructed with an appropriate width and pitch to suitably perform the advancing and anchoring functions in a CTCD 10. The anchor threads 34 have a minor diameter and a major diameter. The preferred anchor section 12 has substantially cylindrical threads 34. Alternatively, the anchor threads 34 may be conical or otherwise increasing or changing in diameter as a function of axial location, but for purposes of this application, the "minor diameter" and "major diameter" of the anchor threads are selected at the axial location of their greatest value, for which most preferred dimensions are set forth below in Table 1. The anchor threads 34 in a preferred embodiment have a pitch in the range of 0.5 to 1.0 mm per rotation.

Since the fragment 30 and the anchor bone 32 are not typically predrilled, the hole for the CTCD 10 in the fragment 30 and anchor bone 32 is not typically pre-tapped. Thus, the anchor threads 34 are preferably self-tapping on the distal side of the anchor section 12, as commonly known in the screw thread art. Having the anchor threads 34 be self-tapping for insertion decreases the number of surgical steps and surgery time as compared to tapping with a separate tap, while providing a firmer attachment with less bone damage and requiring less drill force as compared to not tapping at all.

The CTCD 10 of the present invention is intended to be surgically implanted and left within the patient for a healing duration while the fragment 30 attaches and grows together to the anchor bone 32. During this bone growth healing duration, bone tissue may grow back within the threads cut into the fragment 30 by the anchor threads 34. To assist in removing the anchor section 12 through the fragment 30 after the healing duration, the preferred threads 34 are self-tapping on the proximal side as well. Having the threads 34 be self-tapping on the proximal side reduces the torque necessary for removal, decreasing the likelihood of shearing breakage of the CTCD 10 during removal and decreasing the likelihood of damage to the surrounding bone and surrounding tissue during removal. Having the threads 34 be self-tapping on the proximal side is also quite important for reverse insertion, wherein the proximal side of the CTCD 10 enters the anchor bone 32 first and the CTCD 10 is then pulled back through the anchor bone 32 and bone fragment 30.

As shown in FIG. 2, the preferred anchor threads 34 have a thread form which is angled against pull-out. The angle of the thread form can significantly increase the pull-out force which can be supported by the CTCD 10, which can be very important especially if the anchor bone 32 is weak, damaged or overly porous.

The fragment section 14 has a diameter which is smaller than at least the major diameter of the anchor section 12, and preferably no greater than the minor diameter of the anchor section 12 as well. Being smaller in diameter, the fragment section 14 does not interfere with the hole in the fragment 30 created by the anchor section 12 when the anchor section 12 was advanced through the fragment 30. For instance, the fragment section 14 may have smooth cylindrical profile, contrasted against the threaded anchor section 12. Preferred diameters for the fragment section 14 are set forth below in Table I.

TABLE I

PREFERRED EMBODIMENT DIMENSIONS

| RSSD | RSL | CSOD | CSID | CSL | FSSD | FSL | AOD | AID | ATL | TTL |
|---|---|---|---|---|---|---|---|---|---|---|
| 1.5 | 136 | 1.8 | 1.6 | 15 | 1.5 | 5.5 | 2.5 | 1.8 | 2.5 | 1.5 |
| 1.5 | 126 | 1.8 | 1.6 | 15 | 1.5 | 10 | 2.5 | 1.8 | 8.4 | 2 |
| 1.5 | 91 | 1.8 | 1.6 | 40 | 1.5 | 20 | 2.5 | 1.8 | 8.4 | 2 |
| 1.5 | 119 | 1.8 | 1.6 | 40 | 1.5 | 20 | 2.5 | 1.8 | 8.4 | 2 |
| 1.9 | 118 | 2.3 | 2.0 | 40 | 1.9 | 20 | 3.2 | 2.3 | 8.5 | 2 |
| 1.9 | 78 | 2.3 | 2.0 | 80 | 1.9 | 20 | 3.2 | 2.3 | 8.5 | 2 |
| 2.1 | 118 | 2.6 | 2.2 | 40 | 2.1 | 20 | 3.5 | 2.6 | 9 | 2.5 |
| 2.1 | 78 | 2.6 | 2.2 | 80 | 2.1 | 20 | 3.5 | 2.6 | 9 | 2.5 |
| 2.4 | 117 | 2.9 | 2.5 | 40 | 2.4 | 20 | 4 | 2.9 | 9.5 | 2.5 |
| 2.4 | 77 | 2.9 | 2.5 | 80 | 2.4 | 20 | 4 | 2.9 | 9.5 | 2.5 |
| 2.5 | 116 | 3.1 | 2.7 | 40 | 2.5 | 20 | 4.2 | 3.1 | 10 | 3 |
| 2.5 | 76 | 3.1 | 2.7 | 80 | 2.5 | 20 | 4.2 | 3.1 | 10 | 3 |
| 2.7 | 116 | 3.3 | 2.9 | 40 | 2.7 | 20 | 4.5 | 3.3 | 10 | 3 |
| 2.7 | 76 | 3.3 | 2.9 | 80 | 2.7 | 20 | 4.5 | 3.3 | 10 | 3 |

RSSD: Rotational Section Shaft Diameter
RSL: Rotational Section Length
CSOD: Compression Section Major Diameter
CSID: Compression Section Minor Diameter
CSL: Compression Section Length
FSSD: Fragment Section Shaft Diameter
FSL: Fragment Section Length
AOD: Anchor Major Diameter
AID: Anchor Minor Diameter
ATL: Anchor Thread Length
TTL: Trocar Tip Length
Dimensions are given in mm to two significant digits.

The fragment section 14 thus follows behind the minor diameter on the threaded anchor section 12 and does not substantially engage the bone of the fragment 30. With the small diameter of the fragment section 14, the CTCD 10 of the present invention can be thought of as having a reverse taper, with the proximal fragment section 14 of the CTCD 10 being narrower in diameter than the distal anchor section 12. The reverse taper is particularly important for accurately imparting the proper compression force on the bone fragment 30 during healing.

For larger diameter CTCDs 10, the CTCD 10 may be cannulated. A cannula assists in targeting the CTCD 10 by permitting the CTCD 10 to be placed over a targeting K-wire or bone pin.

The length of the fragment section 14 should approximately correspond with the length of the fragment 30 in the injured bone 20. Obviously, the length of the fragment 30 depends upon the injury, and is not the same for all fractured bones. The CTCD 10 may be provided as part of a kit which allows the surgeon to select the length of the fragment section 14 as desired for a particular fragment 30. For instance, the kit may include bone wires 10 with fragment section lengths which vary in 2 mm increments, i.e., lengths for the fragment section 14 of 2, 4, 6, 8, 10, 12, 14 and 16 mm. More preferably, the length of the CTCD 10 may be convertible by the surgeon as described below, and thus a single length of CRCD 10 may be used for a wide range of fractures, reducing inventory and cost required of the surgeon as well as eliminating any need for the surgeon to measure fragment length and eliminating any possibility that the surgeon could err in measurement or otherwise select the wrong length for the fragment section 14.

The compression section 16 provides a compression engagement 36 which defines the proximal extent of the fragment section 14. The purpose of the compression engagement 36 is to place a compression force on an exterior surface of the bone fragment 30, and thus externally bias the bone fragment 30 toward the anchor bone 32. The compression engagement 36 includes a shoulder 38 extending at a substantial angle to the wire axis for substantial contact with an exterior surface of the bone fragment 30. The CTCD 10 thus allows for compression via the compression engagement 36 after insertion through the skin and placement of the compression engagement 36 against the bone fragment 30.

In the embodiments of FIGS. 1-3 and 7, the compression engagement 36 is provided by one or more nuts 40, 42 placed on a proximal threaded shaft section 44. A preferred length for the proximal threaded shaft section 44 is within the range of about 5 to 80 mm, such as about 15 mm. The preferred compression nut 40 has a compression shoulder section 46 and a drive section 48. The compression shoulder section 46 is on the distal side of the nut 40 and has a cylindrical outer profile, such as an outer diameter of 4 mm, or with an outer diameter which is about 2 mm larger than the shaft diameter of the CTCD 10. The compression shoulder section 46 has an inside bore, which is large enough to fit over both the proximal threaded shaft section 44 and the fragment section 14. For instance, the inside bore may be a smooth cylindrical hole of 1.85 mm diameter for use with a CTCD 10 having 1.5 mm shaft diameters. The length of the compression shoulder section 46 may be designed as desired to correspond with the amount of adjustment and flexibility desired. If kits of bone wires 10 are provided with a 2 mm variance in length of fragment sections 14, then the length of the compression shoulder section 46 may match this variance, i.e., extend axially for at least 2 mm.

The threaded connection between the compression nut 40 and the proximal threaded shaft section 44 provides infinite adjustability of the axial position of the compression nut 40 on the CTCD 10. While other attachment methods may be alternatively used to provide axial adjustability of the compression shoulder section 46 relative to the CTCD 10, a threaded attachment is a relatively low cost and reliable method to provide such adjustability.

The drive section 48 is on the proximal side of the compression nut 40 to enable the surgeon to rotationally advance the compression nut 40 with a standard tool. For instance, for small diameter CTCDs 10, the drive section 48 of the compression nut 40 may have a traditional hexagonal profile with a distance between opposing flats of about 3.45 mm. The drive section 48 is internally threaded to mate with the external threads of the proximal threaded shaft section 44, such as a threaded length of 4 mm. If desired, a lock nut 42 may be further used to secure the compression nut 40 at a desired axial position, such as a lock nut 42 of 2 mm in length. However, the most preferred embodiment omits the lock nut 42, reducing the steps required of the surgeon for proper fixation.

Figure 5:
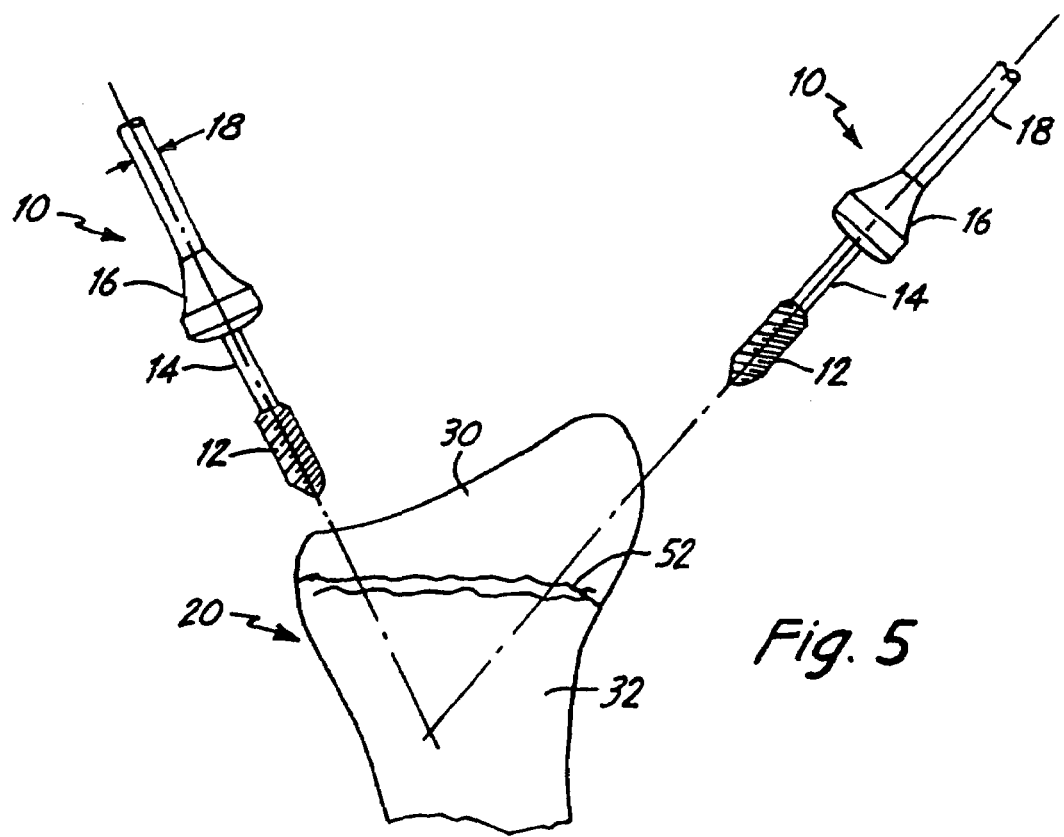
FIG. 5 is a side view of the second embodiment of the invention during implantation with a fractured bone.
Figure 6:
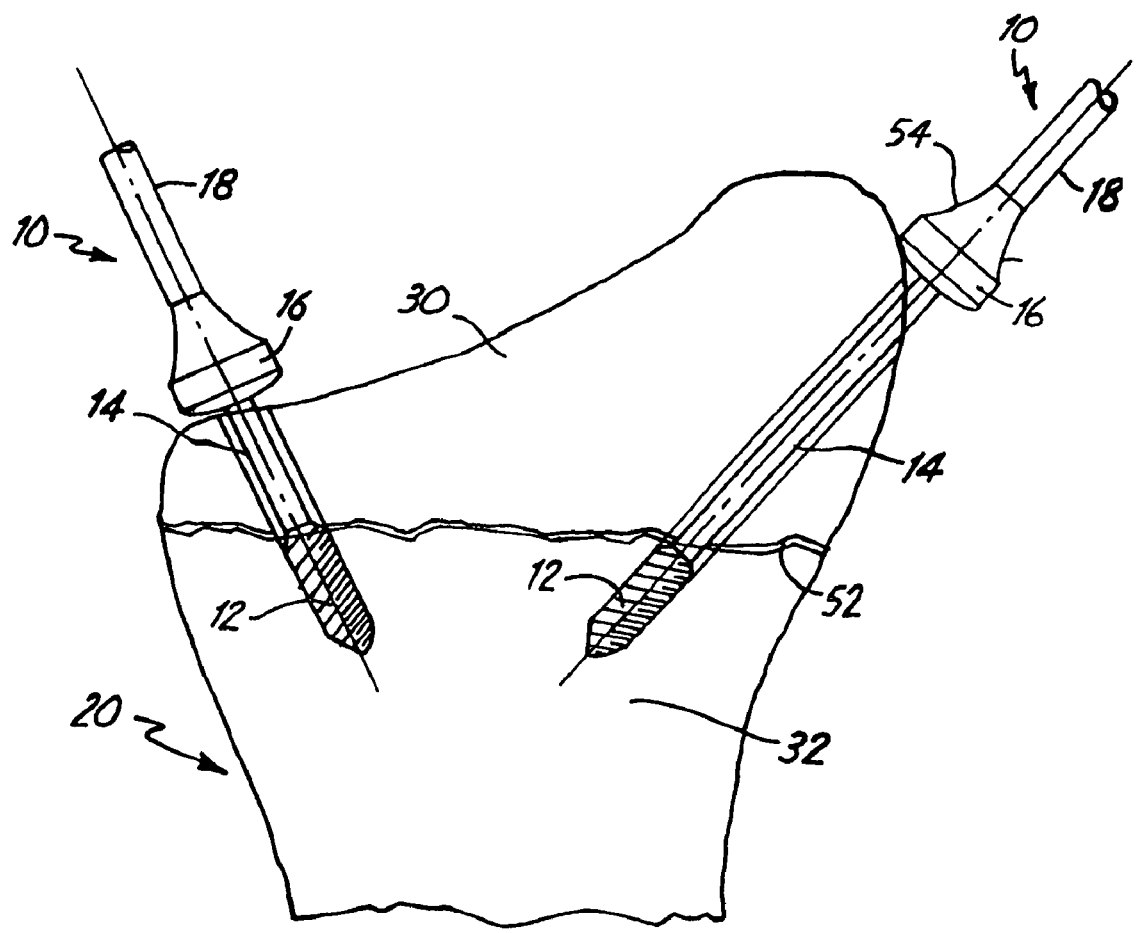
FIG. 6 is a side view of the second embodiment of the invention after implantation.

In the embodiment of FIGS. 4-6, the compression engagement 36 is a tear-drop shoulder 50. If desired, a tear drop shoulder 50 could be placed on the proximal side of the compression nut 40 or lock nut 42. More preferably and in contrast with the compression nut 40, the tear-drop shoulder 50 is integrally formed or permanently affixed to the rest of the CTCD 10.

With either the compression nut 40 or the tear-drop shoulder 50, a distal shoulder surface 38 is provided for contact with the exterior surface of the bone fragment 30. The distal shoulder surface 38 preferably has a curvature of large radius, for enhancing the likelihood of a smooth engagement with the exterior surface of the fragment 30. If desired, the CTCD 10 may be included as part of a kit with several different compression engagements 36 each having a different radius of curvature on the distal shoulder surface 38, enabling the surgeon to pick the compression engagement 36 having a distal shoulder surface 38 which best matches the surface of the bone fragment 30. The intent is to support the compression force with a broad surface to surface contact between the compression engagement 36 and the bone fragment 30 rather than at a point contact which could dig into and damage the bone fragment 30.

Another alternative to adjust to contact surface between the compression engagement 36 and the bone fragment 30 is to place a washer 62 (shown in FIG. 7) between the compression engagement 36 and the bone fragment. The washer 62 can be selected at a size that changes the location and/or areal extent of the compression force place on the bone. If desired, the washer 62 can be selected to have a radius of curvature on its distal side to enable the surgeon to select the shape which best matches the surface of the bone fragment 30. The washer 62 can also be of a different material than the compression engagement 36 and the rest of the CTCD 10, to provide additional compressibility, provide a controlled-release active agent to the wound site, etc. If desired, a collection of washers 62 may be provided to the surgeon in a kit to permit the surgeon to select the best washer 62 for the particular fracture being treated.

Because the fragment section 14 has too small a diameter to positively engage the fragment 30, the compression shoulder 38 provides substantially all of the force pressing the bone fragment 30 into the anchor bone 32 during the healing duration. The present invention permits control of this compression force in either of two ways. First, in the embodiments of FIGS. 1-3 and 4-6, the compression force can be selected by the surgeon by determining how far to rotationally advance the CTCD 10 into the anchor bone 32, while the compression shoulder 38 remains at a constant longitudinal position relative to the CTCD 10. In the embodiment of FIGS. 1-3 and depending upon the relative frictional forces involved, supplying a compression force in this manner may require the surgeon to positively rotate the compression nut 40 during rotation of the CTCD 10. In the embodiment of FIGS. 4-6, the tear-drop shoulder 50 is integrally formed or permanently secured to the CTCD 10, so the surgeon need not take any further steps other than rotating the CTCD 10, and the compression shoulder 38 will always advance with the rotating CTCD 10.

Second, in the embodiments of FIGS. 1-3 and 7, the compression force can be selected by the surgeon after the CTCD 10 is fully advanced into the anchor bone 32, by rotationally advancing the compression nut 40 relative to a stationary CTCD 10. This allows the surgeon to customize the CTCD 10 as to the length between the tip 28 of the CTCD 10 and the compression shoulder 38. Depending upon the relative frictional forces involved, supplying a compression force in this manner may require the surgeon to positively hold the CTCD 10 in a non-rotating position during rotation of the compression nut 40.

With any embodiment, the surgeon can monitor the amount of compression force being applied in any of several different ways. First, the surgeon may be able to visually (either directly or with the aid of scoping equipment) see advancement of the fragment 30 toward the anchor bone 32. Note, for instance, that FIG. 5 shows the fragment 30 separated from the anchor bone 32 by a slight gap 52, and FIG. 6 shows the fragment 30 having been moved against the anchor bone 32 to completely close the gap 52. Second, the surgeon may have the sensitivity to feel the change in torque associated with advancing the compression shoulder 38 against the fragment 30, either by hand or with the aid of a monitoring tool such as a torque wrench. Such "feel" of the advancing torque requirements is relatively easy with the embodiments of FIGS. 1-3 and 7 if the CTCD 10 is stationary; otherwise, the surgeon must be careful to distinguish between any change in torque required to rotationally advance the CTCD 10 as distinguished from any change in torque required to rotationally advance the compression shoulder 38. Third, the amount of torque applied in advancing the compression shoulder 38 can be controlled below a maximum threshold value. Either a drill having a controlled or set maximum torque can be used, or the rotational engagement structure (for instance, the flats of the compression nut 40) can be designed to shear off at a desired torque. In practice, all three methods may be used simultaneously.

The embodiments of FIGS. 1-3 and 7 can provide a further benefit, provided that a proximal threaded shaft section 44 which supports the compression nut 40 is made long enough and of small enough diameter. Namely, the proximal threaded shaft section 44 can be substantially longer than the desired amount of compression movement. Provided the proximal threaded shaft section 44 will fit within the overbore of the fragment 30 created by the anchor section 12, the CTCD 10 may be advanced until a substantial portion of the proximal threaded shaft section 44 resides within the fragment 30. The selectable length of the fragment section 14 is then not as critical. For instance, a preferred length for the proximal threaded shaft section 44 in the embodiment of FIGS. 1-3 is 15 mm, while the preferred compression nut 40 together with the lock nut 42 have an axial length of only 8 mm. Provided the diameter of the proximal threaded shaft section 44 permits it to fit within the overbore drilled by the anchor section 12, then up to 7 mm of the proximal threaded shaft section 44 can be placed within the overbore in the fragment 30. The compression nut 40 can be advanced until at least the compression shoulder section 46 extends over the fragment section 14, i.e., axially for 2 mm beyond the end of the proximal threaded shaft section 44, for a total range of compression motion for the compression shoulder 38 of 9 mm. With this large range of compression motion for the compression shoulder 38, the kit need only include fragment sections 14 with a length variance of the total range of compression motion, e.g, a kit with fragment sections 14 of 2, 11 and 20 mm would allow use on a fragment 30 of anywhere from 0 to 27 mm in thickness. If the length of the proximal threaded shaft section 44 was lengthened to 33 mm, then a single CTCD 10 with a fragment section 14 of 2 mm could be used on fragments 30 of 0 to 27 mm in thickness.

However, the tradeoff for this flexibility in length lies in the strength of the CTCD 10. In particular, if the fragment section 14 has a diameter of 1.5 mm, then the major diameter of the proximal threaded shaft section 44 should be 1.5 mm or less to fit within the overbore in the fragment 30 to the same extent as the fragment section 14 fits within the overbore. If the thread depth is retained at at least 0.15 mm, and major diameter of 1.5 mm results in a minor diameter of no greater than 1.2 mm. However, the minor diameter must be strong enough to support the required torque to drive the anchor section 12 through the fragment 30 and through the anchor bone 32. With current materials, a minor diameter of 1.2 mm over a 33 mm length results in a brittle, weak product, which is likely to break off during driving through the bone 20 or during use.

Instead, the preferred embodiments of the CTCD 10 retain a minimum diameter of at least 1.5 mm throughout. For 1.5 mm embodiments, the major diameter of the proximal threaded shaft section 44 is accordingly selected at 1.83 mm. This major diameter interferes with the minor diameter of 1.65 mm drilled by the "thin" anchor section 12, and hence the CTCD 10 should be used without advancing any part of the proximal threaded shaft section 44 into the fragment bore. Given that no part of the proximal threaded shaft section 44 extends into the fragment bore, the compression nut 40 only has 2 mm of axial advancement flexibility, and the CTCDs 10 are thus provided in kits of 2 mm variance in length of fragment sections 14. The major diameter for the proximal threaded shaft section 44 of 1.83 mm does not interfere with the minor diameter of 1.85 mm drilled by the "thick" anchor section 12. As such, the proximal threaded shaft section 44 can extend into the fragment bore drilled by the "thick" anchor section 12, and the compression nut 40 in the preferred "thick" embodiment has a full 9 mm of axial advancement flexibility.

The greatest flexibility of compression movement would be provided by having the proximal threaded shaft section 44 extend fully up to the anchor section 12, and having little or no length of fragment section 14. However, the smooth surface of the fragment section 14 prevents bone ingrowth and makes the CTCD 10 more easily removed than simply having the entire length threaded. Workers skilled in the art will appreciate that there is no medical purpose achieved by fully threading the fragment section 14, because every bone fragment has some thickness. Thus, the preferred embodiments all have a fragment section length of at least 2 mm. For purposes of this invention, if the CTCD 10 is threaded fully up to the anchor section 12, the distal 2 mm of the machine thread form should be considered to be the fragment section 14.

Further, the flexibility of compression movement provided by having the proximal threaded shaft section 44 fit within the overbore created by the anchor section 12 needs should be understood within the context of the material with which the CTCD 10 is being used. For porous, unhealthy bone, the proximal threaded shaft section 44 may fit within the overbore created by the anchor section 12 merely by having the major diameter of the proximal threaded shaft section 44 be less than the major diameter of the anchor section 12 (CSOD<AOD). Even if the major diameter of the proximal threaded shaft section 44 is greater than the minor diameter of the anchor section 12, (i.e., CSOD>AID) such that there is some interference between the internal threads cut into the bone by the anchor section 12 and the threads of the proximal threaded shaft section 44), the bone fragment/proximal threaded shaft section interference may be sufficiently small due to the weakened nature of the bone that it can be overcome by the compression force. More preferably, the minor diameter of the proximal threaded shaft section 44 is also less than the minor diameter of the anchor section 12 (i.e., CSID<AID). Even more preferably, the major diameter of the proximal threaded shaft section 44 is no greater than the mean diameter of the anchor section 12 (i.e., CSOD<=(AID+AOD)/2), thus ensuring minimal interference between the bone fragment 30 and the proximal threaded shaft section 44 such than any interference can be overcome even in healthy, cortical bone. Even more preferably, the major diameter of the proximal threaded shaft section 44 is no greater than the minor diameter of the anchor section 12 (i.e., CSOD<=AID), such that there is no interference between the opening in the fragment section and the proximally threaded shaft section 44.

The rotation section 18 of the CTCD 10 extends substantially beyond the end of the compression section 16. In many uses, the rotation section 18 will extend outside the patient's skin during the entire healing duration, which can greatly facilitate bone healing. The rotation section 18 allows the CTCD 10 to be used in fixating the fracture with a fixator support structure as described in U.S. Pat. Nos. 6,058,748, 6,283,946, 6,652,524 and U.S. patent application Ser. Nos. 10/233,897 and 10/699,213, incorporated by reference, which can allow the proper amount of stress to be placed on the bone 20 during healing, substantially benefitting the healing process. The fixator support structure attaches to the rotation section 18 of the CTCD 10. The placement of the compression shoulder 38 against the fragment 30 also increases the fixation by reducing wire toggle, such as may occur during wrist motion. The rotation section 18 allows the CTCD 10 to be rotated without interference with tissue adjacent the bone 20, so the surrounding tissue is less damaged during surgery than occurred with prior art methods. In one preferred embodiment, the rotation section 18 is cylindrical with a diameter of 1.5 mm, and extends for 100 to 150 mm.

The length of the rotation section 18 relative to the length of the entire CTCD 10 is a significant variable to ensure that the rotation section 18 can be used for its desired purpose, as is the length of the bone exterior section 24 relative to the length of the entire CTCD 10. Table II expresses the ratios of length of rotation section 18 and length of the bone exterior section 24 relative to the length of the entire CTCD 10 for the preferred embodiments.

TABLE II

Rotation and Bone Exterior Section Length Ratios

| RSSD | RSL | BESL | Total | RSLR | BESLR |
|------|-----|------|-------|------|-------|
| 1.5  | 136 | 151  | 161   | 84%  | 94%   |
| 1.5  | 126 | 141  | 161   | 78%  | 88%   |
| 1.5  | 91  | 131  | 161   | 57%  | 81%   |
| 1.5  | 119 | 159  | 189   | 63%  | 84%   |
| 1.9  | 118 | 158  | 189   | 62%  | 84%   |
| 1.9  | 78  | 158  | 189   | 41%  | 84%   |
| 2.1  | 118 | 158  | 189   | 62%  | 84%   |
| 2.1  | 78  | 158  | 189   | 41%  | 84%   |
| 2.4  | 117 | 157  | 189   | 62%  | 83%   |
| 2.4  | 77  | 157  | 189   | 41%  | 83%   |
| 2.5  | 116 | 156  | 189   | 61%  | 83%   |

TABLE II-continued

Rotation and Bone Exterior Section Length Ratios

| RSSD | RSL | BESL | Total | RSLR | BESLR |
|------|-----|------|-------|------|-------|
| 2.5  | 76  | 156  | 189   | 40%  | 83%   |
| 2.7  | 116 | 156  | 189   | 61%  | 83%   |
| 2.7  | 76  | 156  | 189   | 40%  | 83%   |

RSSD: Rotational Section Shaft Diameter
RSL: Rotational Section Length
BESL: Bone Exterior Section Length
Total: Total Length of CTCD
RSLR: Rotational Section Length Ratio as percentage of Total Length
BESLR: Bone Exterior Section Length Ratio as percentage of Total Length As can be seen by this rotation section length ratio analysis, the rotation section 18 in each case makes up more than a third of the total length of the CTCD 10, and more preferably 40% or more of the total length of the CTCD 10. These length ratios ensure that a sufficient length of rotation section 18 is provided that the CTCD 10 can be percutaneously manipulated without substantial interference from the patient's tissue. Workers skilled in the art will appreciate that the same rotation section length ratios could be effectively achieved even if the entire length of the rotation section 18 was threaded identically with the compression section 16. Thus, as can be seen by this analysis of bone exterior section length ratios, the bone exterior section 24 in each case makes up more than a third of the total length of the CTCD 10, and more preferably more than half of the total length of the CTCD 10, and even more preferably more than 75% of the total length of the CTCD 10.

The present invention includes several features which are specifically directed to removal of the CTCD 10 after the healing duration. In contrast to most bone pins and bone screws, the CTCD 10 of the present invention leaves a significant length exposed through the skin to grasp for removal without damaging tissue. In the embodiment of FIGS. 1-3, the threads of the proximal threaded shaft section 44 have a different pitch and a different shape than the anchor threads 34. For instance, the proximal threaded shaft section 44 may have a pitch of 0.4 mm per revolution, as compared to the preferred anchor thread pitch of 0.5 to 1.0 mm. Counterclockwise rotation of the CTCD 10 will cause the CTCD 10 to retract its anchor thread pitch, i.e., 0.5 to 1.0 mm per revolution. Because the proximal threaded shaft section 44 has a shallower pitch than the anchor threads 34, the nut(s) 40, 42 must retract with counterclockwise rotation of the CTCD 10. That is, the nut(s) 40, 42 could rotate with the rotating CTCD 10, in which case the nut(s) 40, 42 would retract at the anchor thread pitch, i.e., 0.5 to 1.0 mm per revolution. Alternatively, even if the surrounding tissue has grown around the nut(s) 40, 42 and prevents rotation of the nut(s) 40, 42, the nut(s) 40, 42 will still back out at the difference between pitches, i.e., 0.1 mm to 0.6 mm per revolution of the CTCD 10. Further, if the compression nut 40 rotates all of the way to the distal end of the proximal threaded shaft section 44, the compression nut screw thread has a smaller inside diameter than the outside diameter of the fragment section 14 (at least at a proximal side of the fragment section 14), preventing the compression nut 40 from further advancing onto the fragment section 14.

As shown in FIG. 3, the proximal threaded shaft section 44 may have a thread form which is balanced in both proximal and distal directions, in contrast to the preferred anchor threads 34 which have a thread form which is angled against pull-out. Alternatively, the thread form for the proximal threaded shaft section 44 may be angled oppositely to the thread form of the preferred anchor threads 34, to better support the compression force placed on the compression nut 40.

In the embodiment of FIGS. 4-6, the proximal surface 54 of the tear-drop shoulder 50 assists in removal of the CTCD 10 through tissue which may grown around the bone exterior section 24 of the CTCD 10 during the healing duration. In particular, the proximal surface 54 of the tear-drop shape is sloped for removal, with the slope angle being shallow near the axis of the CTCD 10, becoming steeper at intermediate diameters, and then again becoming shallow near the maximum diameter of the tear-drop shoulder 50. This shape helps to separate the overlying tissue with minimal damage to such surrounding tissue when the CTCD 10 is removed. In the embodiments of FIGS. 1-3 and 7, the proximal surface of the compression nut 40 and/or the lock nut 42 could alternatively be modified to provide a similar slope for assisting in separating overlying tissue during removal.

Because of the various features of the CTCD 10 of the present invention which facilitate removal, removal of the CTCD 10 can be accomplished without requiring a separate incision to be made after the healing duration. Avoiding this additional incision greatly helps in healing the tissue over the fractured bone 20, both in terms of the length of time required for full healing and in terms of avoiding the build-up of scar tissue.

Figure 7:
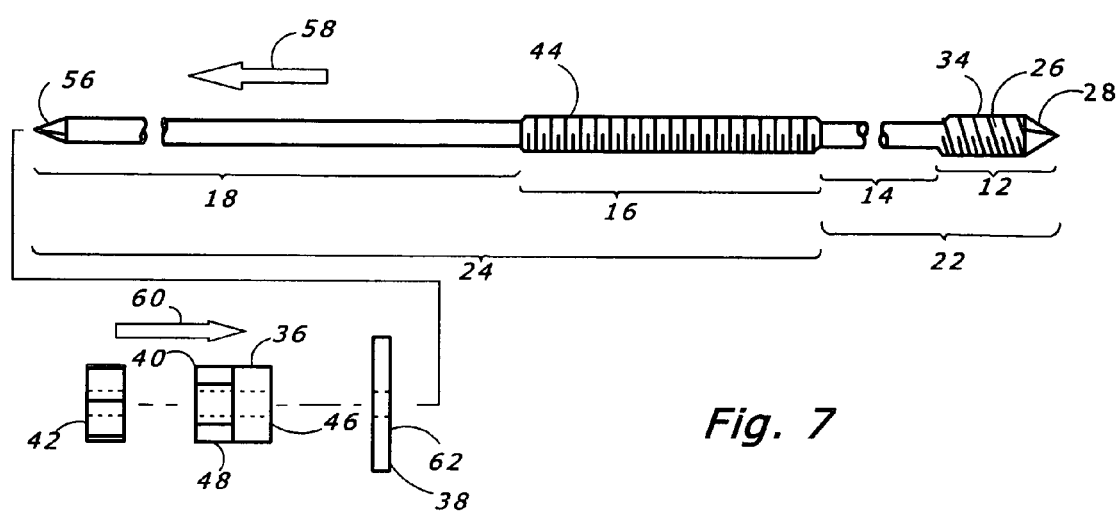
FIG. 7 is a side view assembly drawing of a third embodiment modified to permit reverse fixation.

The CTCD 10 is designed to permit forward fixation to the bone. In some embodiments, only forward fixation may be used, and the proximal end of the rotation section 18 may be squared off. Alternatively as shown in FIG. 7, the CTCD 10 may be designed for reverse fixation, useful in such cases as correcting digit or extremity (e.g., toe) deformity. For reverse fixation, a pointed trocar tip 56 is provided on the proximal end of the rotation section 18.

The CTCD 10 may be formed out of any surgically acceptable strong material, such as surgical acceptable stainless steel (such as 316 LVM, per ASTM F1350 or ASTM F138, electropolished and passivated) or a titanium alloy (such as TI-6AL-4V, per ASTM F136). The CTCD 10 might also be formed out of a bioresorpable material if a sufficiently strong bioresorbable material is selected, or if holes in the bone are pre-drilled and/or pre-tapped.

The typical method of use of the CTCD 10 of the present invention to repair a fractured bone should be readily apparent from the preceding discussion, and will be further outlined here. Insertion of the CTCD 10 is performed through a small incision with blunt dissection carried to the bone 20. For insertion, the CTCD 10 is drilled through the fragment 30, and the thicker diameter anchor threads 34 overbore a hole through the fragment 30. Drilling through a sheath (not shown) helps protect surrounding tissue so that the threads 34 do not damage nearby soft tissue.

Once the anchor threads 34 are secured within the fragment 30, the surgeon may optionally use the CTCD 10 to manipulate the fragment 30. With the bone anchor section 12 advanced into the bone fragment 30, the bone exterior section 24 extends significantly beyond the patient's tissue. The surgeon may grasp the bone exterior section 24 in a "joystick" fashion to reposition or bias the bone fragment 30 relative to the anchor bone 32. This "joysticking" method of manipulating the bone fragment 30 is particularly appropriate for larger diameter CTCDs 10, which can support significant forces and moments applied to the bone fragment 30 without bending or breaking.

Once the surgeon has used the CTCD 10 to manipulate the bone fragment 30 into the desired healing location relative to the anchor bone 32, the surgeon further screws the CTCD 10 such that the bone anchor section 12 advances into the anchor bone 32 with the fragment section 14 in the bone fragment 30. Again because of the length of the bone exterior section 24 extending beyond the patient's tissue, the surgeon can hold the bone exterior section 24 in a desired alignment while screwing into the anchor bone 32.

The thicker diameter anchor threads 34 then reach the anchor bone 32 and pull the CTCD 10 axially forward. Once the narrower fragment section 14 of the CTCD 10 extends through the fragment 30, the CTCD 10 is no longer in threaded engagement with the fragment 30. The CTCD 10 is preferably advanced until the anchor section 12 is fully within the anchor bone 32. This places the fragment section 14 sufficiently forward that the fragment section 14 extends through the bone fragment 30 without threaded engagement with the bone fragment 30.

The CTCD shown in FIG. 7 can be used for forward fixation with the procedure described for FIGS. 1-3, or can be used for reverse fixation, in which case a modified procedure is used. For reverse fixation, the CTCD 10 is introduced proximal end 56 first to the back side of the anchor bone 32, and back driven through the anchor bone 32 in the direction shown by arrow 58 in FIG. 7. The proximal end 56 of the CTCD 10 is driven through the anchor bone 32 until the proximal end 56 of the CTCD 10 extends out of the fragment 30. Once the rotation section 18 of the CTCD 10 is accessible out of the fragment 30, a drill can be secured to the rotation section 18 of the CTCD 10 and driven in reverse direction and pulled back (in the direction shown by arrow 58) until the anchor threads 34 reverse cut through the anchor bone 32. Not only are anchor threads 34 preferably self-tapping on the proximal side of the anchor section 12, but the compression threads 44 may also be self-tapping on the proximal side of the compression section 16 to assist in pulling through the anchor bone. Once the CTCD 10 is reverse driven and pulled back to a final desired location, the compression shoulder 36 of the nut 40 can be axially advanced in the direction shown by arrow 60 to its desired compression location on the CTCD 10 and relative to the bone fragment 30.

In its fully advanced and final position, the compression engagement 36 is in substantial contact with an exterior surface of the bone fragment 30 to bias the bone fragment 30 toward the anchor bone 32. In the embodiments of FIGS. 1-3 and 7 in which the compression engagement 36 is axially movable on the CTCD 10, the compression nut 40 can be tightened with a wrench until the compression shoulder 38 engages the exterior surface of the fragment 30. Specifically, the surgeon may advance the CTCD 10 by screwing the CTCD 10 forward until the anchor section 12 is fully seated in its final position within the anchor bone 32, and then, with the CTCD 10 stationary, screw or otherwise move the compression engagement 36 axially on the elongated shaft to position the compression engagement 36 in an axial position to make contact with an exterior surface of the bone fragment 30 with the desired compression force. Alternatively, in the embodiments of FIGS. 1-3 and 7 with forward fixation, the surgeon may select the desired axial placement of the compression nut 40 on the CTCD 10 and position the nut 40 in that position, and then advance the compression engagement 36 to the substantial contact position as part of advancing the anchor section 12 within the anchor bone 32. If the compression engagement 36 is integrally attached on the CTCD 10 such as in the case of the preferred tear-drop shoulder 50, then the compression engagement 36 is advanced to this substantial contact position merely by advancing the anchor section 12 within the anchor bone 32. In either case, the CTCD 10 may be used to axially move the fragment 30 toward the anchor bone 32 to reduce or eliminate the gap 52 prior to achieving the desired compression force If desired, after the compression engagement 40, 50 is in its position making substantial biasing contact pressing the bone fragment 30 to the anchor bone 32, the bone exterior section 24 may be cut, sheared off or otherwise shortened proximal to the compression engagement 40, 50. Such a cutting or shearing act can shorten the CTCD 10 so it no longer resides outside the patient's tissue during the healing duration. Shortening of the CTCD 10 after complete advancement into the anchor bone 32 is particularly appropriate for healing modalities wherein the primary purpose of the CTCD 10 was to enable "joysticking" of the bone fragment 30, without any desired attachment of an external fixator.

Further, if the bone exterior section 24 is properly clipped within the proximal threaded shaft section 44, it will deform the thread form and act to lock the compression nut 40 onto the CTCD 10. Thus, if the CTCD 10 is clipped sufficiently close to the compression nut 40, the clipping step effectively converts the CTCD 10 from a variable length device to a fixed length device. The compression nut 40 cannot advance axially on the CTCD 10 because it is in tight contact with the bone. The compression nut 40 cannot retract axially on the CTCD 10 because the deformed thread form at the cut prevents further rotation of the compression nut 40. The CTCD 10 is converted into a fixed length lag bolt at the exact length selected in situ within the fracture by the surgeon.

If desired, the bone exterior section 24 may include a section of reduced thickness (not shown) to facilitate the shortening act. If desired, the section of reduced thickness can be designed to withstand a set torque before shearing off, such that the surgeon drives the CTCD 10 forward into the anchor bone 32 until the compression engagement 36 resists further screwing with sufficient torque to shear off the proximal side of the bone exterior section 24 at the section of reduced thickness. However, pre-selecting the location of cutting will prevent the surgeon from selecting the exact length in situ as described above.

For any embodiment which will be used with cutting or separating, the CTCD 10 should include structure which will not be cut off which can transmit removal torque. For instance, the flats on compression nut 40 may allow the surgeon to apply torque for removal of the CTCD 10 after the healing duration, and even after the major length of the bone exterior section 24 of the CTCD 10 has been cut off.

After the healing duration, the CTCD 10 is simply removed from the bone 20 by counterclockwise rotation of the CTCD 10, perhaps by applying reverse torque on the rotation section 18. Particularly in embodiments having sloped profile on the proximal side of the compression engagement 36, the sloped profile assist in separating tissue, causing as little additional tissue damage as possible.

The present invention can be used on most types of fractures which have previously been treated by percutaneous pinning. Avulsion fractures of the hand and foot as well reconstruction procedures such as IP fusions and hammertoe correction are excellent applications. The joysticking treatment method can be applied to a wide variety of fractures, making the CTCD 10 easier to implant into a fracture than traditional bone screws.

Although the present invention has been described with reference to preferred embodiments, workers skilled in the art will recognize that changes may be made in form and detail without departing from the spirit and scope of the invention. In particular, the specific dimensions mentioned but not required by the claims are exemplary only, and do not limit the claimed invention. Similarly, while the present invention has been described with regard to bone fracture fixation, the CTCD 10 has many fastener applications outside the orthopaedic arts, particularly when access to and/or movement of the fragment relative to the anchor substrate is limited, and also when predrilling is not advisable and/or possible. For example, an excellent application of the CTCD 10 would be to repair wood which is in the process of splitting, such as in furniture or cabinetry.

The invention claimed is:

1. A method of repairing a fractured bone, comprising:
    screwing a device through a bone fragment, the device comprising:
        an elongated shaft having a bone penetration section extending distally from a bone exterior section about a shaft axis, the bone penetration section being shorter than the bone exterior section, the bone penetration section including a fragment section and a bone anchor section located distally to the fragment section, the bone anchor section having threads with a major diameter of the threads being greater than a diameter of the fragment section; and
        a compression engagement on a distal end of the bone exterior section, the compression engagement providing a shoulder extending at a substantial angle to the shaft axis, the shoulder being wider than the major diameter of the threads of the bone anchor section;
    further screwing the device such that the bone anchor section advances into an anchor bone with the fragment section in the bone fragment and with the bone exterior section extending outside the bone with a length extending outside the bone longer than the bone penetration section, with the compression engagement in contact with an exterior surface of the bone fragment to provide a compressive force on the bone fragment toward the anchor bone; and
    moving the compression engagement axially on the elongated shaft to position the compression engagement in an axial position to make substantial contact with an exterior surface of the bone fragment when the bone anchor section is advanced to a final position;
    wherein the screwing act and the further screwing act occur in a reverse direction such that the device is inserted into the anchor bone prior to engaging the bone fragment, while moving the compression engagement axially on the elongated shaft occurs in a forward direction, opposite to the direction the device was introduced to the bone.

* * * * *